US010123897B2

(12) United States Patent
Sutti et al.

(10) Patent No.: US 10,123,897 B2
(45) Date of Patent: Nov. 13, 2018

(54) DYNAMIC CUSHION HEEL-ANKLE-FOOT ORTHOSIS

(71) Applicant: Kinematic Improvements LLC, Plano, TX (US)

(72) Inventors: Nathan Joseph Sutti, Plano, TX (US); Franck Vautrin, Dallas, TX (US); Jeff Robbins, Aubrey, TX (US)

(73) Assignee: Kinematic Improvements, LLC, Plano, TX (US)

( * ) Notice: Subject to any disclaimer, the term of this patent is extended or adjusted under 35 U.S.C. 154(b) by 331 days.

(21) Appl. No.: 15/133,167

(22) Filed: Apr. 19, 2016

(65) Prior Publication Data
US 2016/0278961 A1 Sep. 29, 2016

Related U.S. Application Data

(63) Continuation of application No. 14/859,107, filed on Sep. 18, 2015.
(Continued)

(51) Int. Cl.
| | |
|---|---|
| *A61F 5/00* | (2006.01) |
| *A61F 5/01* | (2006.01) |
| *A61H 3/00* | (2006.01) |
| A61H 1/02 | (2006.01) |
| A61H 3/04 | (2006.01) |

(52) U.S. Cl.
CPC .......... *A61F 5/0111* (2013.01); *A61F 5/0127* (2013.01); *A61H 3/00* (2013.01); *A61F 2005/0137* (2013.01); *A61F 2005/0165* (2013.01); *A61F 2005/0179* (2013.01); *A61F 2005/0197* (2013.01); *A61H 1/0266* (2013.01); *A61H 3/04* (2013.01); *A61H 2003/007* (2013.01); *A61H 2201/0119* (2013.01); *A61H 2201/164* (2013.01); *A61H 2201/165* (2013.01); *A61H 2201/1635* (2013.01)

(58) Field of Classification Search
CPC ...... A61F 2005/0137; A61F 2005/0165; A61F 2005/0179; A61F 2005/0197; A61H 2003/007; A61H 2201/0019; A61H 2201/1635; A61H 2201/164; A61H 2201/165
See application file for complete search history.

(56) References Cited

U.S. PATENT DOCUMENTS

| | | | | |
|---|---|---|---|---|
| 4,934,355 A | * | 6/1990 | Porcelli | A61F 5/0127 602/16 |
| 9,326,880 B2 | * | 5/2016 | Szczepanski | A61F 5/0127 |

(Continued)

FOREIGN PATENT DOCUMENTS

WO   WO 02065942 A2 * 8/2002 ............ A61F 5/0111

*Primary Examiner* — Kim M Lewis
(74) *Attorney, Agent, or Firm* — Mohr Intellectual Property Law Solutions, P.C.

(57) ABSTRACT

A dynamic cushion heel-ankle-foot orthosis system is configured to provide controlled tibial progression in a human user. The dynamic cushion heel-ankle-foot orthosis system includes a leg calf shell further comprising a leg calf shell plantar flexion ridge at a lowermost point. A boot shell is rotatably connected to the leg calf shell and further comprising a boot shell plantar flexion ridge at an uppermost point. The boot shell plantar flexion ridge contacts the leg calf shell plantar flexion ridge at a plantar flexion ridges region and rotates no further.

10 Claims, 9 Drawing Sheets

Related U.S. Application Data

(60) Provisional application No. 62/138,535, filed on Mar. 26, 2015.

(56) References Cited

U.S. PATENT DOCUMENTS

| | | | |
|---|---|---|---|
| 2014/0066829 A1* | 3/2014 | Drillio | A61F 5/0127 602/27 |
| 2016/0135978 A1* | 5/2016 | McGovern | A61F 5/0127 602/27 |
| 2017/0112233 A1* | 4/2017 | Morag | A43B 13/186 |

* cited by examiner

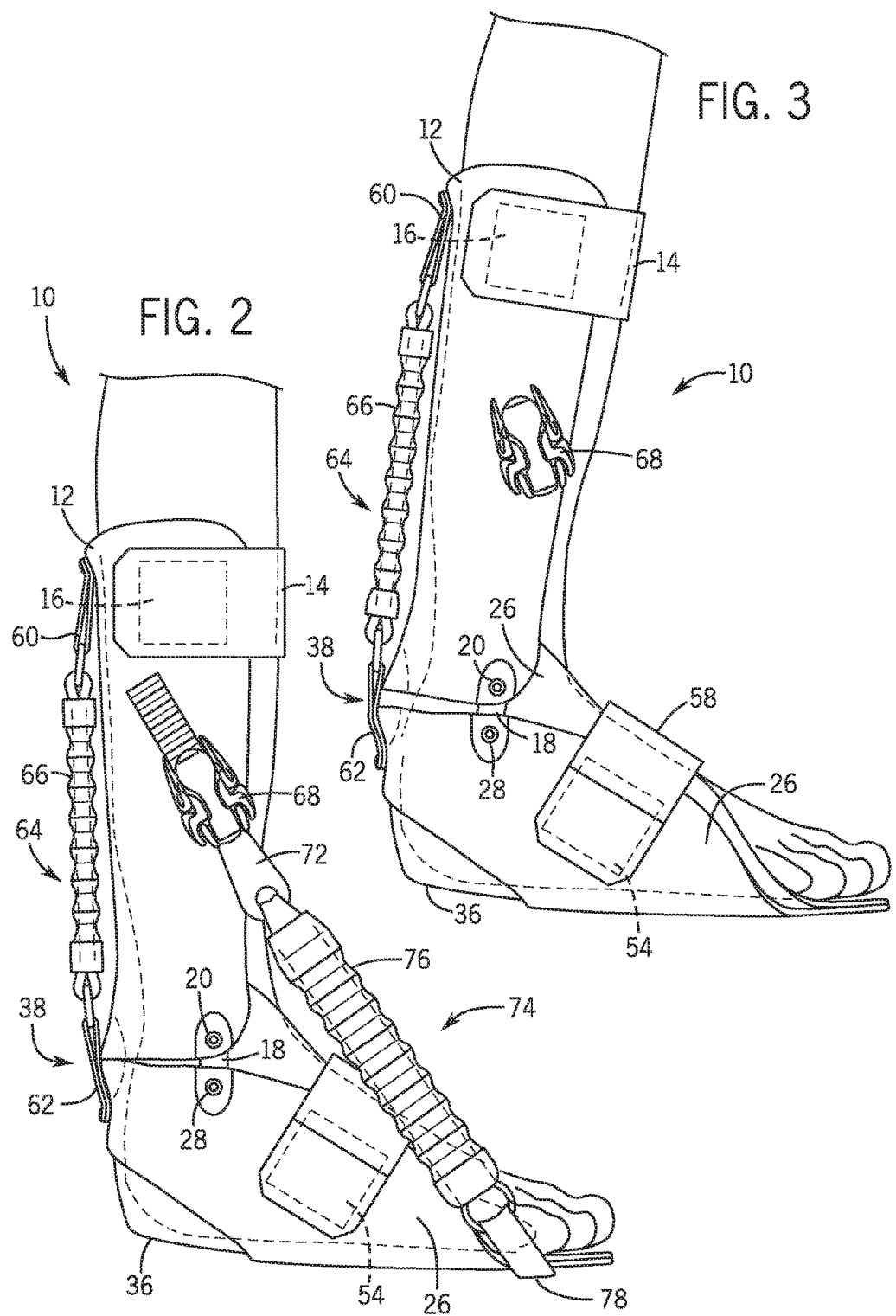

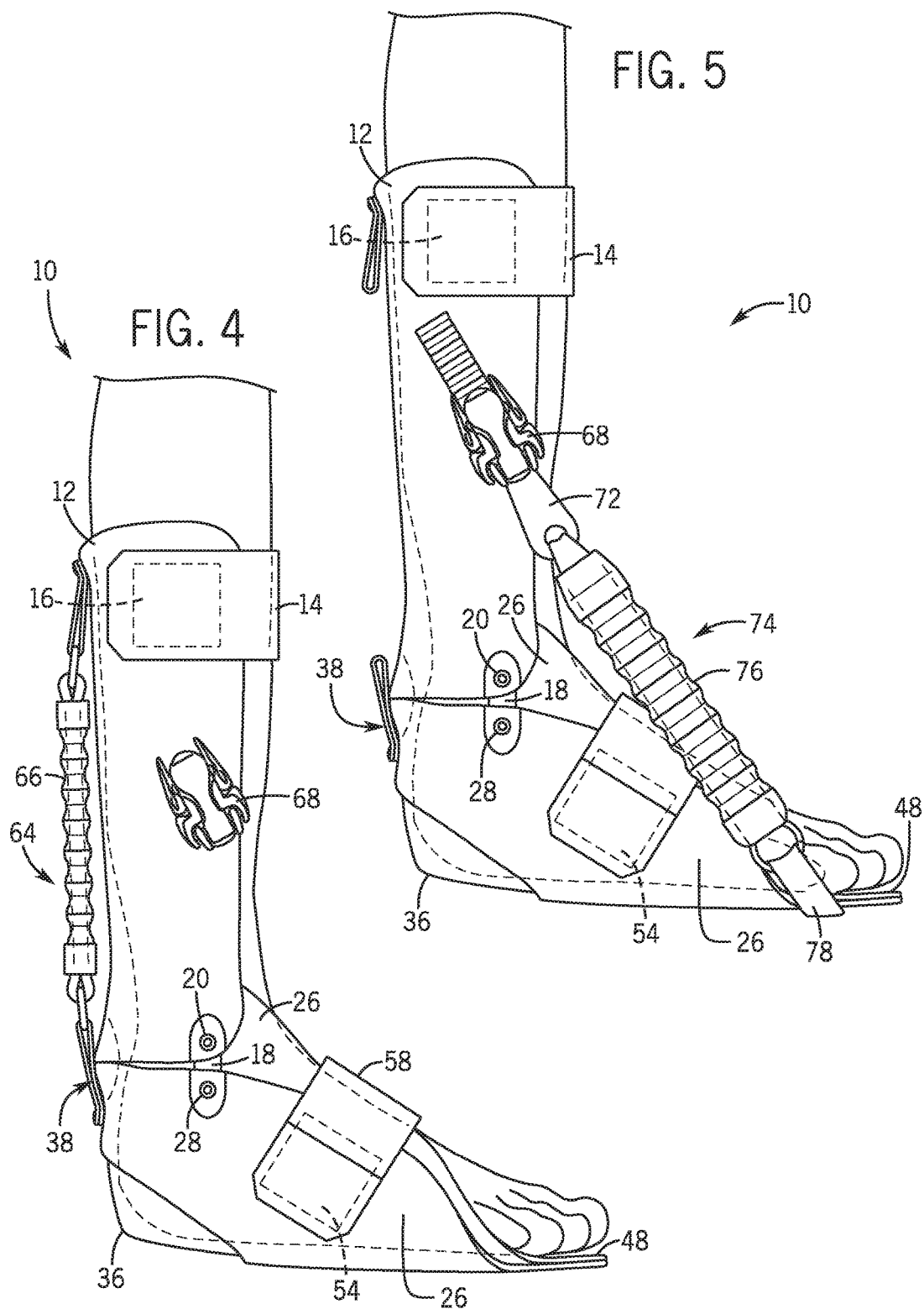

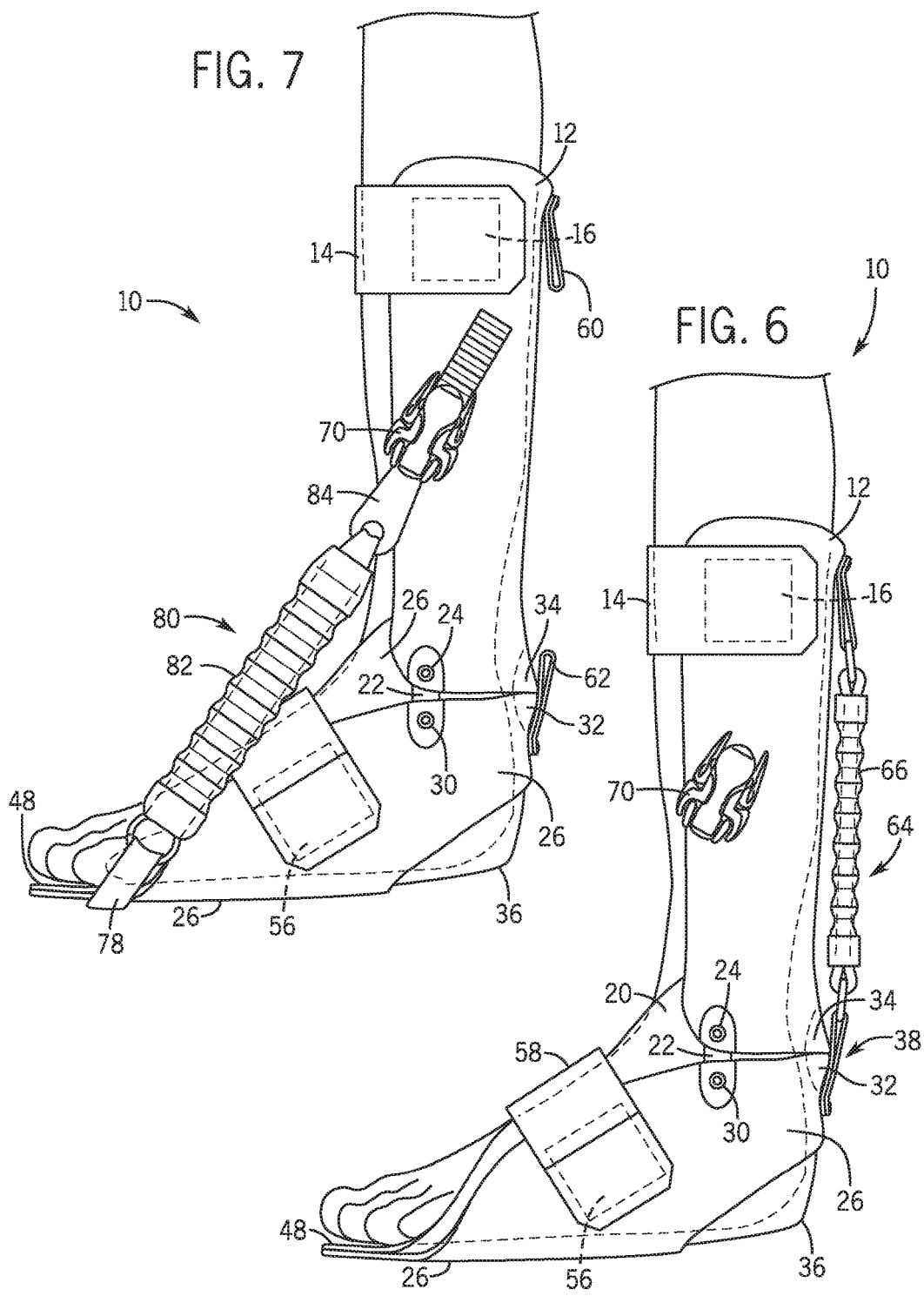

DYNAMIC CUSHION HEEL-ANKLE-FOOT ORTHOSIS

RELATED APPLICATION

This application is a continuation-in-part of non-provisional U.S. patent application Ser. No. 14/859,107 filed on Sep. 18, 2015, which, in turn, claims priority to provisional patent application U.S. Ser. No. 62/138,535 filed on Mar. 26, 2015. The entire contents of both applications are herein incorporated by reference.

BACKGROUND

The embodiments herein relate generally to medical equipment and an orthosis and/or prosthesis.

Patients that require the use of an orthosis often present with sagittal instabilities which require the use of a plantar flexion stop built into the device. These patients may also present with complications to controlling tibial progression and may also have limited range of motion. The problem for these patients is that when a plantar flexion stop is used, within the orthosis, the stop creates an abrupt knee flexion moment at the initial part of gait which is not part of normal kinematics. Furthermore, a stop is often required in such cases as plantar flexion contractures or those that hyperextend the knee. The problem can be summed up in saying that there is no device available to the public that allows controlled tibial progression, decreases plantarflexion moment at initial contact, decrease contractures and provides a means of stretching contracted muscles, which can be used for both ambulation and therapeutic applications. Embodiments of the disclosed invention solve these problems.

SUMMARY

A dynamic cushion heel-ankle-foot orthosis system is configured to provide controlled tibial progression in a human user. The dynamic cushion heel-ankle-foot orthosis system includes a leg calf shell further comprising a leg calf shell plantar flexion ridge at a lowermost point. A boot shell is rotatably connected to the leg calf shell and further comprising a boot shell plantar flexion ridge at an uppermost point. The boot shell plantar flexion ridge contacts the leg calf shell plantar flexion ridge at a plantar flexion ridges region and rotates no further.

In some embodiments, a heel portion can be joined to the boot shell wherein the heel portion further comprises an outer layer fused to an inner layer. A cushion layer can be between the outer layer and the inner layer. A carbon foot plate can be fused to a portion of the outer layer.

In some embodiments, a first fastener portion and a second fastener portion can be attached to the boot shell. An upper can be attached to the first fastener portion and the second fastener portion.

In some embodiments, an upper connection loop, can be attached to a back portion of the leg calf shell. A lower connection loop can be attached to the boot shell. A posterior stretch cord assembly, can be connected to the upper connection loop and the lower connection loop.

In some embodiments, the posterior stretch cord assembly can include a hollow cord, partially filled with a first retainer end and a second retainer end. A posterior stretch cord sheath can be slid over hollow cord. A first ring and a second ring can be connected to the posterior stretch cord sheath. A first clip and a second clip can be wrapped around the posterior stretch cord sheath. A first rubber sleeve can be covering the first clip. A second rubber sleeve can be covering the second clip.

In some embodiments, a first buckle and a second buckle can be attached to the leg calf shell. A first connector strap can be adjustably connected to the first buckle. A first anterior stretch cord assembly can be attached to the first connector strap. A first anterior stretch cord sheath can be covering the first anterior stretch cord assembly. A flat stretch cord can be attached to the first anterior stretch cord assembly. A second anterior stretch cord assembly can be attached to the flat stretch cord. A second anterior stretch cord sheath can be covering the second anterior stretch cord assembly. A second connector strap can be attached to the second anterior stretch cord assembly and the second buckle.

BRIEF DESCRIPTION OF THE FIGURES

The detailed description of some embodiments of the invention is made below with reference to the accompanying figures, wherein like numerals represent corresponding parts of the figures.

FIG. 2 shows a side elevation view perspective view of one embodiment of the present invention;

FIG. 3 shows a side elevation view perspective view of one embodiment of the present invention;

FIG. 4 shows a side elevation view of one embodiment of the present invention;

FIG. 5 shows a side elevation view of one embodiment of the present invention;

FIG. 6 shows a side elevation view of one embodiment of the present invention;

FIG. 7 shows a side elevation view of one embodiment of the present invention;

DETAILED DESCRIPTION OF CERTAIN EMBODIMENTS

Figure 1:
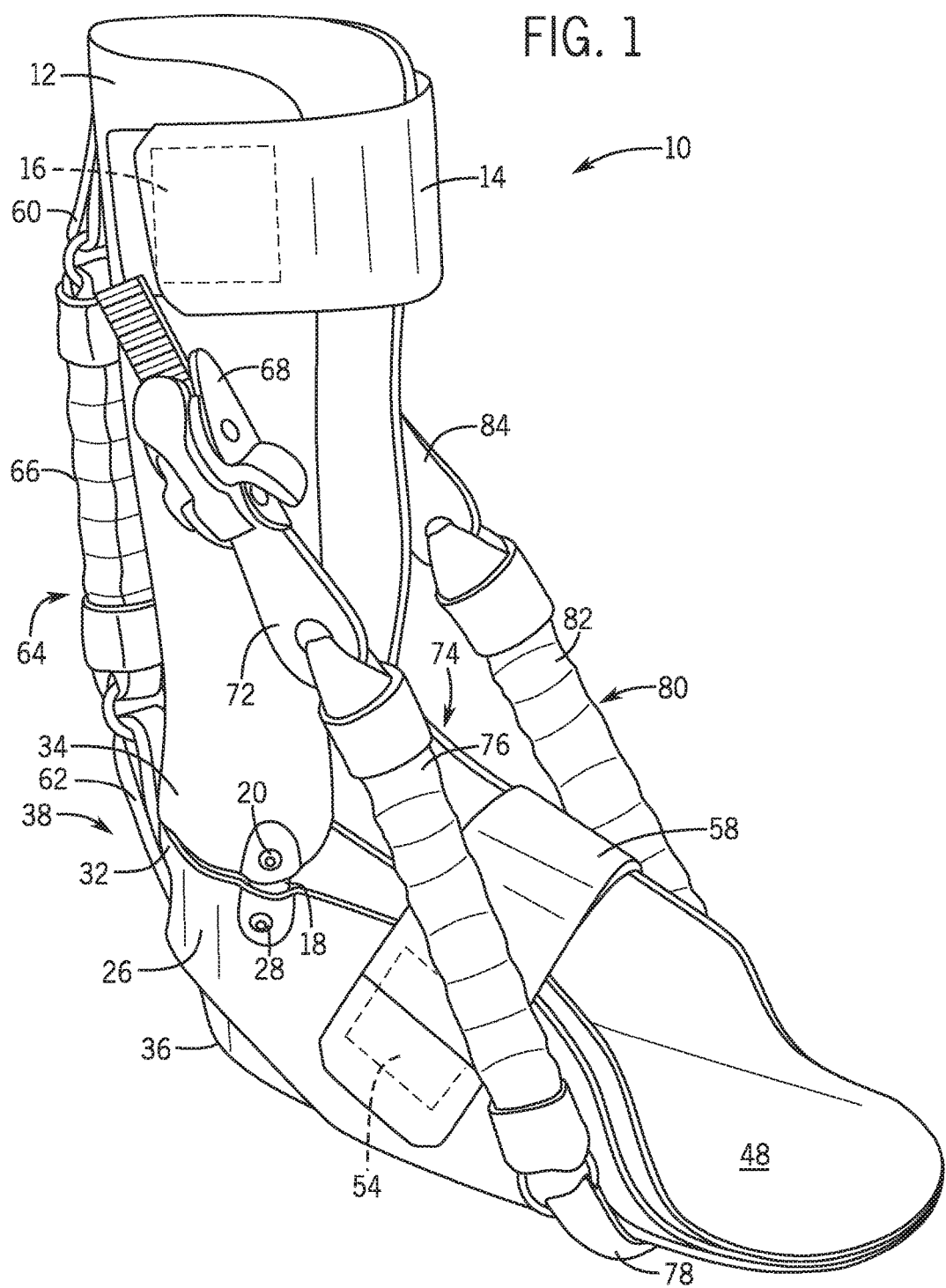
FIG. 1 shows a side front perspective view of one embodiment of the present invention.

By way of example, and referring to FIG. 1, one embodiment of dynamic cushion heel-ankle-foot orthosis 10 comprises leg calf shell 12 attached to leg strap 14 with hook and loop fastener 16. Leg calf shell 12 is attached to first connecting member 18 with first connecting member first fastener 20. Leg calf shell 12 is further attached to second connecting member 22 with second connecting member first fastener 24. First connecting member 18 is further attached to boot shell 26 with first connecting member second fastener 28. Second connecting member 22 is further attached to boot shell 26 with second connecting member second fastener 30.

The upper most point of boot shell 26 is boot shell plantar flexion ridge 32. The lower most point of leg calf shell 12 is leg calf shell plantar flexion ridge 34. When leg calf shell 12 is rotated toward heel portion 36 (which is counter clockwise in FIGS. 1-4 and clockwise in FIGS. 6-7), boot shell plantar flexion ridge 32 contacts leg calf shell plantar flexion ridge 34 at a plantar flexion ridges region 38 and rotates no further in that direction.

Turning to FIGS. 11-14, heel portion 36 further comprises outer layer 40 fused to inner layer 42. In some embodiments, cushion layer 44 can be inserted between outer layer 40 and inner layer 42. In some embodiments, carbon foot plate 46 is fused to a portion of outer layer 40. In some embodiments, cushion layer 44 can be the outermost lawyer with other layers as described above.

Figure 9:
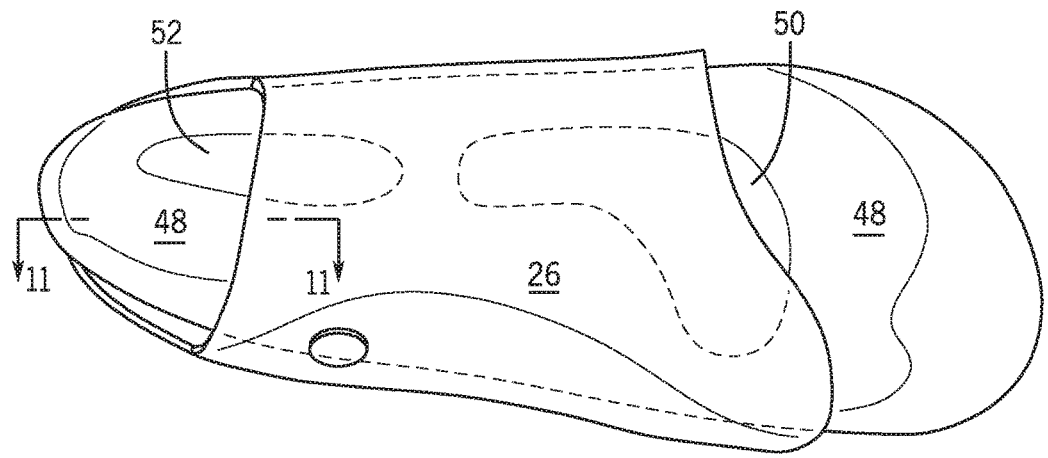
FIG. 9 shows a bottom plan view of one embodiment of the present invention.
Figure 10:
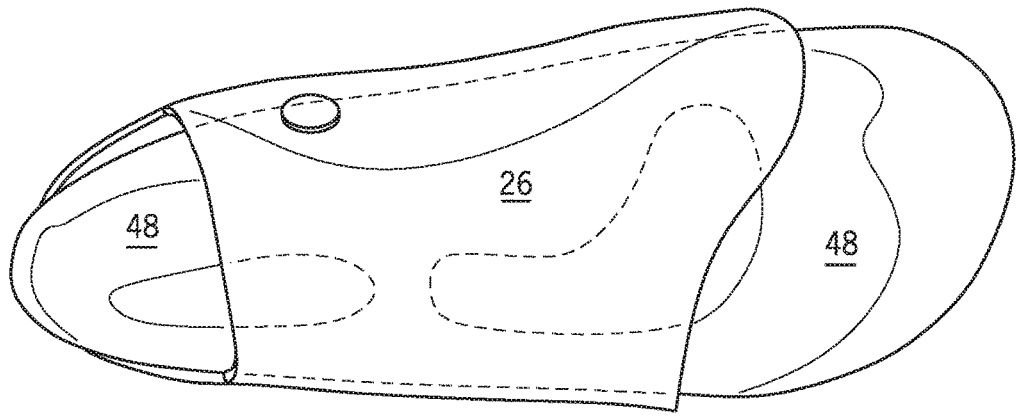
FIG. 10 shows a bottom plan view of one embodiment of the present invention.
Figure 11:
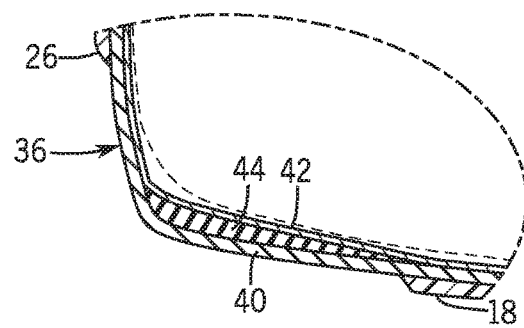
FIG. 11 shows a section view of one embodiment of the present invention along line 11-11 in FIG. 9.
Figure 12:
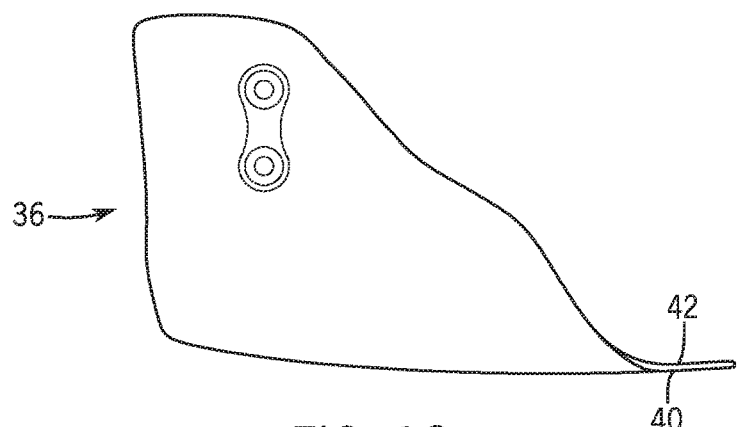
FIG. 12 shows a detail side elevation view of one embodiment of the present invention.
Figure 13:
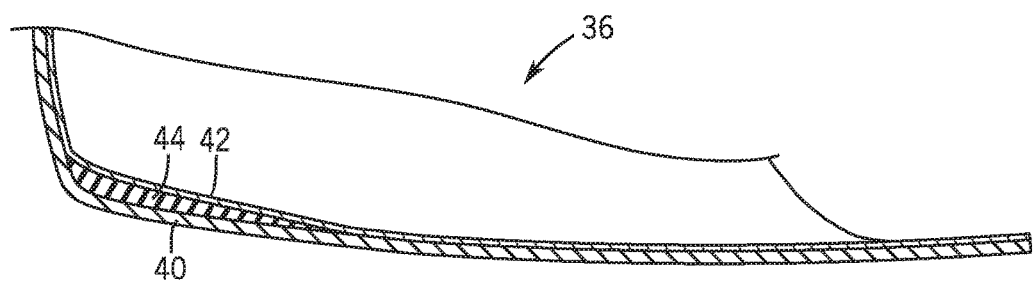
FIG. 13 shows a section view of one embodiment of the present invention.
Figure 14:
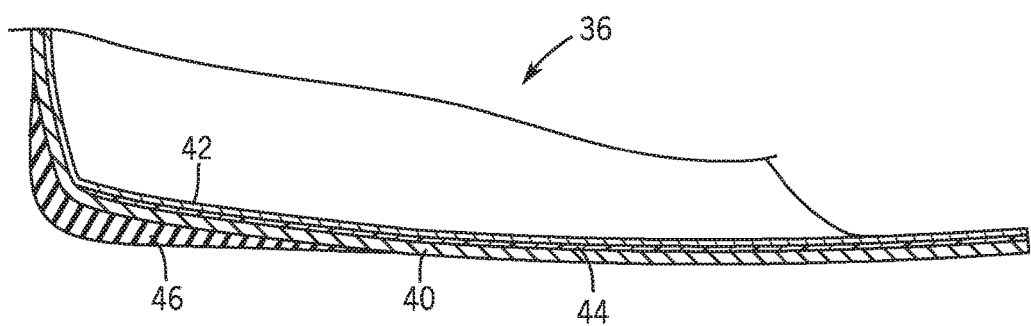
FIG. 14 shows a section view of one embodiment of the present invention.
Figure 15:
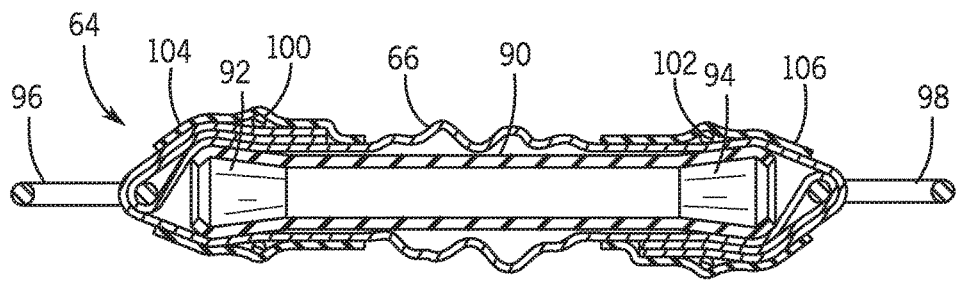
FIG. 15 shows a process step in constructing one embodiment of the stretch cord assembly of one embodiment of the present invention.

Turning to FIGS. 9-10, inner layer 42 is covered with padding layer 48. In some embodiments, additional padding 50, 52 can be used depending on the needs of the user.

As shown in FIGS. 1-7, boot shell 26 is attached to first fastener portion 54 and second fastener portion 56. First fastener portion 54 and second fastener portion 56 are attached to upper 58. In some embodiments, first fastener portion 54 and second fastener portion 56 can be hook fasteners and a loop fastener can be attached to upper 58. Generally, it is preferable that upper 58 be adjustable.

A back portion of leg calf shell 12 is attached to upper connection loop 60. Boot shell 26 is attached to lower connection loop 62. Upper connection loop 60 is joined to lower connection loop 62 with posterior stretch cord assembly 64 which is covered with posterior stretch cord sheath 66.

Leg calf shell 12 is attached to first buckle 68 and second buckle 70. First buckle 68 is adjustably connected to first connector strap 72. First connector strap 72 is attached to first anterior stretch cord assembly 74 covered with first anterior stretch cord sheath 76. First anterior stretch cord assembly 74 is attached to flat stretch cord 78. Flat stretch cord 78 is attached to second anterior stretch cord assembly 80 covered with first anterior stretch cord sheath 82. Second anterior stretch cord assembly 80 is attached to second connector strap 84. Second connector strap 84 is connected to second buckle 70.

Figure 8:
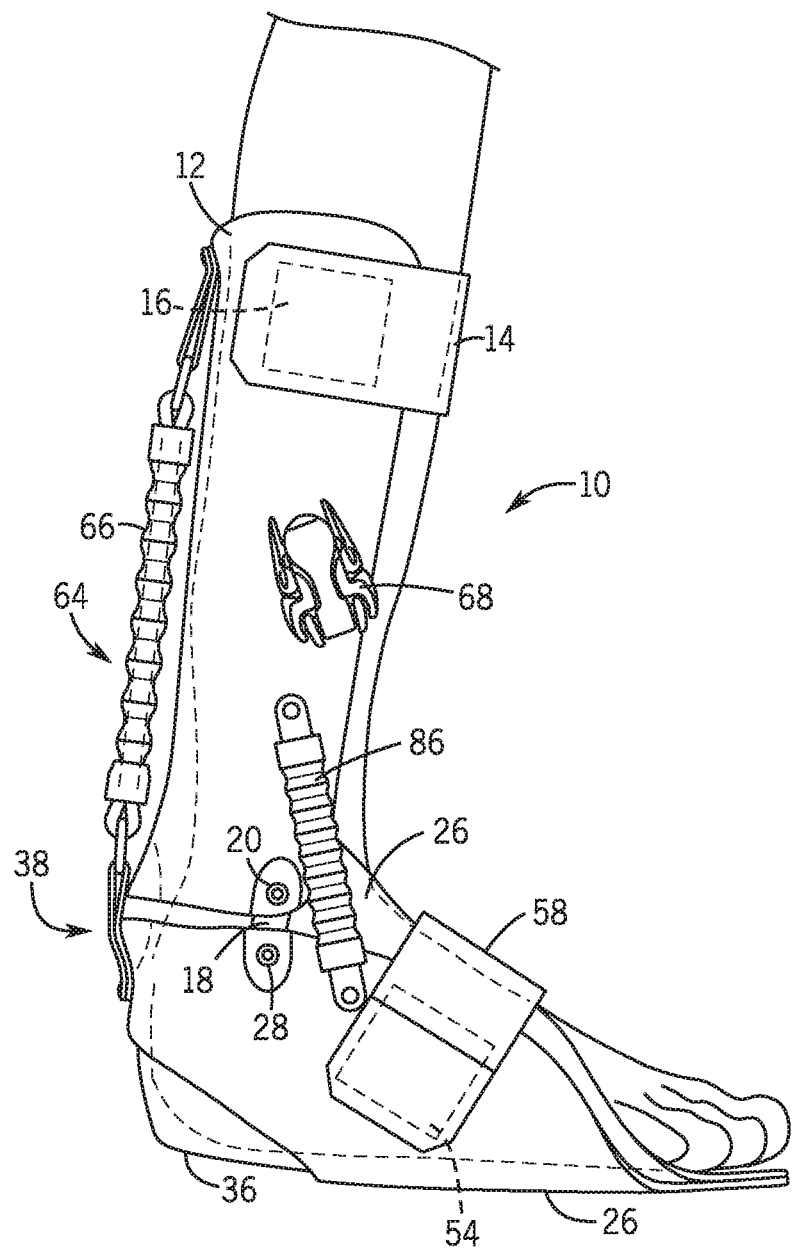
FIG. 8 shows a side elevation view of one embodiment of the present invention.

This construction is not exclusive. As shown in FIG. 8, direct attachment cord 86 can be used without regard for buckles or a flat stretch cord.

Figure 16:
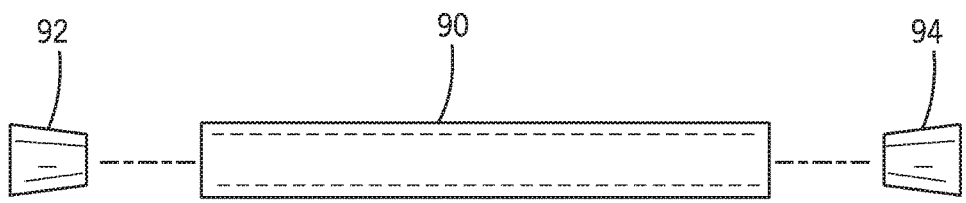
FIG. 16 shows a process step in constructing one embodiment of the stretch cord assembly of one embodiment of the present invention.
Figure 17:
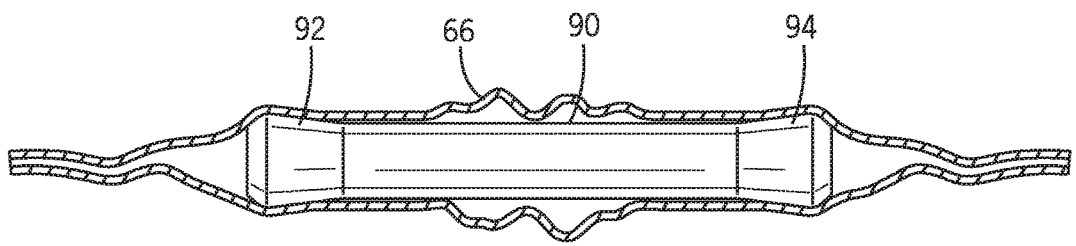
FIG. 17 shows a process step in constructing one embodiment of the stretch cord assembly of one embodiment of the present invention.
Figure 18:
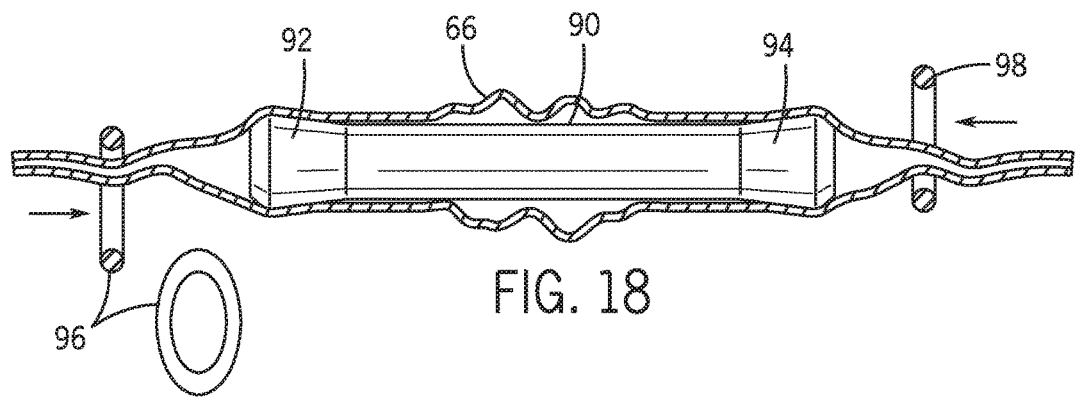
FIG. 18 shows a process step in constructing one embodiment of the stretch cord assembly of one embodiment of the present invention.
Figure 19:
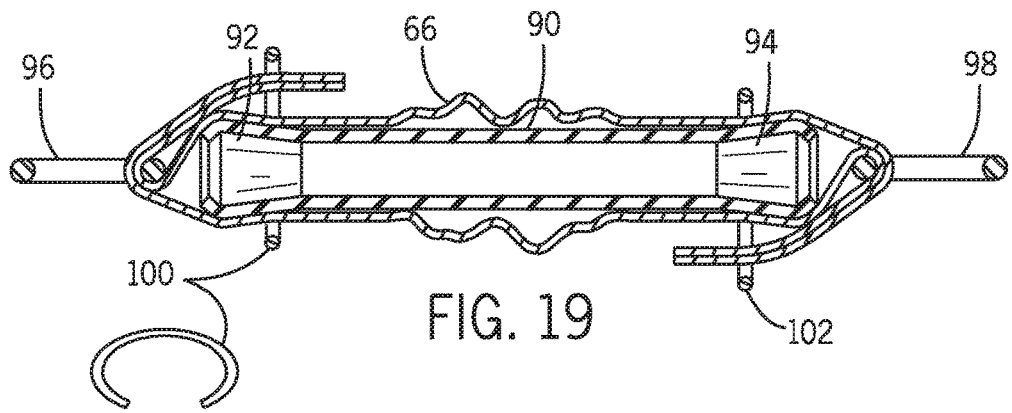
FIG. 19 shows a process step in constructing one embodiment of the stretch cord assembly of one embodiment of the present invention.
Figure 20:
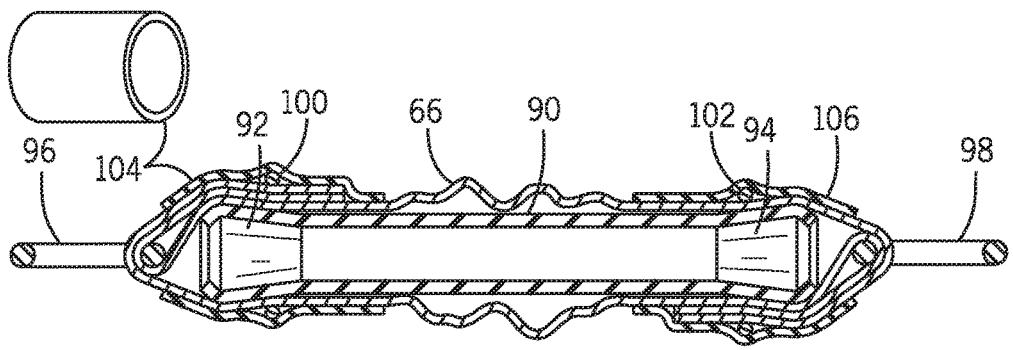
FIG. 20 shows a process step in constructing one embodiment of the stretch cord assembly of one embodiment of the present invention.
Figure 21:
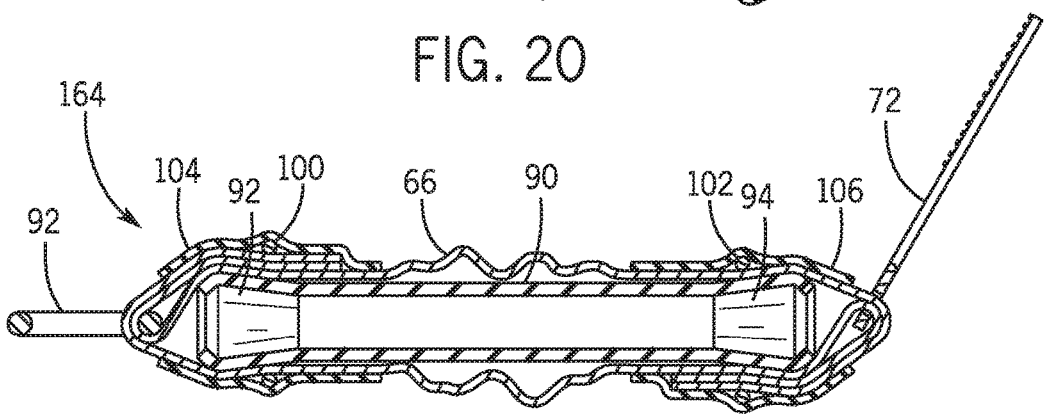
FIG. 21 shows a section view of the stretch cord assembly of one embodiment of the present invention.
Figure 22:
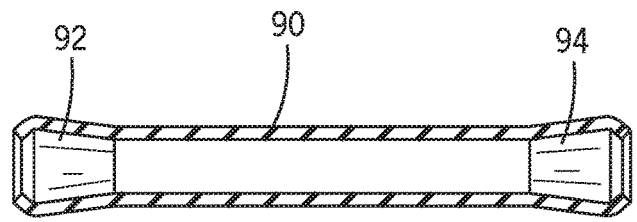
FIG. 22 shows a process step in constructing one embodiment of the stretch cord assembly of one embodiment of the present invention.

Turning to FIGS. 15-21 a process for making stretch cord assembly 64 includes the following steps, which are not necessarily in order. First, as shown in FIG. 16, providing hollow cord 90. Then, inserting first retainer end 92 and second retainer end 94 into hollow cord 90. Turning to FIG. 22, hollow cord 90 is wrapped around first retainer end 92 and second retainer end 94. As shown in FIG. 17, posterior stretch cord sheath 66 is slid over hollow cord 90. As shown in FIG. 18, posterior stretch cord sheath 66 is wrapped around first ring 96 and second ring 98. Turning to FIG. 19, posterior stretch cord sheath 66 is then held in place with first clip 100 and second clip 102. As shown in FIG. 20, first clip 100 is then covered with first rubber sleeve 104 and second clip 102 is then covered with second rubber sleeve 106. In some embodiments of stretch cord assembly 164, second ring 98 is replaced with first connector strap 72.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A dynamic cushion heel-ankle-foot orthosis system configured to provide controlled tibial progression in a human user; the dynamic cushion heel-ankle-foot orthosis system comprising:

a leg calf shell further comprising a leg calf shell plantar flexion ridge at a lowermost point a boot shell, rotatably connected to the leg calf shell and further comprising a boot shell plantar flexion ridge at an uppermost point; wherein the boot shell plantar flexion ridge contacts the leg calf shell plantar flexion ridge at a plantar flexion ridges region and rotates no further;

a heel portion joined to the boot shell, wherein the heel portion further comprises an outer layer fused to an inner layer;

a first buckle and a second buckle, attached to the leg calf shell;

a first connector strap, adjustably connected to the first buckle;

a first anterior stretch cord assembly, attached to the first connector strap;

a first anterior stretch cord sheath, covering the first anterior stretch cord assembly;

a flat stretch cord, attached to the first anterior stretch cord assembly;

a second anterior stretch cord assembly, attached to the flat stretch cord;

a second anterior stretch cord sheath, covering the second anterior stretch cord assembly;

a second connector strap, attached to the second anterior stretch cord assembly and the second buckle.

2. The dynamic cushion heel-ankle-foot orthosis system of claim 1, further comprising a cushion layer between the outer layer and the inner layer.

3. The dynamic cushion heel-ankle-foot orthosis system of claim 1, further comprising a carbon foot plate fused to a portion of the outer layer.

4. The dynamic cushion heel-ankle-foot orthosis system of claim 1 further comprising:

a first fastener portion and a second fastener portion attached to the boot shell; and an upper attached to the first fastener portion and the second fastener portion.

5. The dynamic cushion heel-ankle-foot orthosis system of claim 1 further comprising:

an upper connection loop, attached to a back portion of the leg calf shell;

a lower connection loop attached to the boot shell;

a posterior stretch cord assembly, connected to the upper connection loop and the lower connection loop.

6. The dynamic cushion heel-ankle-foot orthosis system of claim 5, wherein the posterior stretch cord assembly further comprises:

a hollow cord, partially filled with a first retainer end and a second retainer end;

a posterior stretch cord sheath, slid over hollow cord;

a first ring and a second ring, connected to the posterior stretch cord sheath;

a first clip and a second clip, wrapped around the posterior stretch cord sheath;

a first rubber sleeve, covering the first clip; and a second rubber sleeve, covering the second clip.

7. A dynamic cushion heel-ankle-foot orthosis system configured to provide controlled tibial progression in a human user; the dynamic cushion heel-ankle-foot orthosis system comprising:

a leg calf shell further comprising a leg calf shell plantar flexion ridge at a lowermost point a boot shell, rotatably connected to the leg calf shell and further comprising a boot shell plantar flexion ridge at an uppermost point; wherein the boot shell plantar flexion ridge contacts the leg calf shell plantar flexion ridge at a plantar flexion ridges region and rotates no further;

a heel portion joined to the boot shell, wherein the heel portion further comprises an outer layer fused to an inner layer;

an upper connection loop, attached to a back portion of the leg calf shell;

a lower connection loop attached to the boot shell; and a posterior stretch cord assembly, connected to the upper connection loop and the lower connection loop;

wherein the posterior stretch cord assembly further comprises:

a hollow cord, partially filled with a first retainer end and a second retainer end;

a posterior stretch cord sheath, slid over hollow cord;

a first ring and a second ring, connected to the posterior stretch cord sheath;

a first clip and a second clip, wrapped around the posterior stretch cord sheath;

a first rubber sleeve, covering the first clip; and a second rubber sleeve, covering the second clip.

8. The dynamic cushion heel-ankle-foot orthosis system of claim 7, further comprising a cushion layer between the outer layer and the inner layer.

9. The dynamic cushion heel-ankle-foot orthosis system of claim 7, further comprising a carbon foot plate fused to a portion of the outer layer.

10. The dynamic cushion heel-ankle-foot orthosis system of claim 7 further comprising:

a first fastener portion and a second fastener portion attached to the boot shell; and an upper attached to the first fastener portion and the second fastener portion.

\* \* \* \* \*